United States Patent
Pyo et al.

(10) Patent No.: US 7,880,022 B2
(45) Date of Patent: Feb. 1, 2011

(54) METHOD FOR SEPARATION AND PURIFICATION OF 13-DEHYDROXYBACCATIN III AND 10-DEACETYLPACLITAXEL FROM TAXANS-CONTAINING MATERIALS

(75) Inventors: Sang-Hyun Pyo, Daejeon (KR); Jin-Suk Cho, Daejeon (KR); Moon-Suk Kim, Daejeon (KR); Bong-Kyu Song, Daejeon (KR); Ho-Joon Choi, Daejeon (KR)

(73) Assignee: Samyang Genex Corporation, Seoul (KR)

( * ) Notice: Subject to any disclaimer, the term of this patent is extended or adjusted under 35 U.S.C. 154(b) by 700 days.

(21) Appl. No.: 11/560,005

(22) Filed: Nov. 15, 2006

(65) Prior Publication Data
US 2007/0112207 A1    May 17, 2007

(30) Foreign Application Priority Data
Nov. 17, 2005    (KR) ............... 10-2005-0110407

(51) Int. Cl.
C07D 305/00    (2006.01)
(52) U.S. Cl. .................... 549/510; 549/511
(58) Field of Classification Search ............ 549/519, 549/511
See application file for complete search history.

(56) References Cited

U.S. PATENT DOCUMENTS

| | | | | |
|---|---|---|---|---|
| 5,256,801 A | * | 10/1993 | Carver et al. | 549/510 |
| 5,279,949 A | * | 1/1994 | Nair | 435/123 |
| 5,900,367 A | | 5/1999 | Hong et al. | |
| 6,066,748 A | * | 5/2000 | Han et al. | 549/510 |
| 6,878,832 B2 | * | 4/2005 | Saiji | 549/510 |
| 6,881,852 B2 | * | 4/2005 | Sharma et al. | 549/510 |
| 7,259,268 B2 | * | 8/2007 | Pyo et al. | 549/510 |

FOREIGN PATENT DOCUMENTS

| | | |
|---|---|---|
| KR | 10-2001-0072758 | 7/2001 |
| KR | 10 2004 0060832 A | 6/2004 |

* cited by examiner

*Primary Examiner*—Janet L. Andres
*Assistant Examiner*—Raymond Covington
(74) *Attorney, Agent, or Firm*—Lexyoume IP Group, PLLC (57) ABSTRACT

This invention is directed to a method for efficiently separating and purifying 13-dehydroxybaccatin III and 10-deacetylpaclitaxel with a high purity of 90% or higher purity, preferably 99.5% or higher purity, from taxane-containing materials such as *Taxus* species, and the thusly obtained highly pure 13-dehydroxybaccatin III and 10-deacetylpaclitaxel can be used as semi-synthetic precursors of paclitaxel and/or docetaxel that are anticancer agents.

5 Claims, 8 Drawing Sheets

METHOD FOR SEPARATION AND PURIFICATION OF 13-DEHYDROXYBACCATIN III AND 10-DEACETYLPACLITAXEL FROM TAXANS-CONTAINING MATERIALS

CROSS REFERENCE TO RELATED APPLICATION

This application claims priority to and the benefit of Korean Patent Application No. 10-2005-0110407 filed on Nov. 17, 2005, which is hereby incorporated by reference for all purposes as if fully set forth herein.

BACKGROUND OF THE INVENTION (a) Field of the Invention

The present invention relates to a method of separating and purifying 13-dehydroxybaccatin III and 10-deacetylpaclitaxel with high purity of 90% or higher purity, preferably 99.5% or higher purity, from taxane-containing materials, and the thusly obtained highly pure 13-dehydroxybaccatin III and 10-deacetylpaclitaxel can be used as semi-synthetic precursors of paclitaxel and/or docetaxel that are useful anticancer agents.

(b) Description of the Related Art 13-dehydroxybaccatin III and 10-deacetylpaclitaxel are precursors that can be converted into paclitaxel or docetaxel by chemical reactions. Since paclitaxel was a result from large-scale screening programs for antitumoral substances by U.S. National Cancer Institute in 1960s, it has been known as one of the most important anticancer substance for ovarian cancer, breast cancer, etc., and therefore, it has been widely used with the approval by U.S. Food and Drug Administration (FDA) in 1992. However, as this substance is isolated and purified from the bark of yew, which contains substance in a very small amount as low as 0.02%, the separation and purification of the substance are very costly, and furthermore, it becomes one of the factors in the destruction of resource and ecosystem.

In order to overcome such drawbacks, methods of semi-synthesizing paclitaxel by using baccatin III or 10-deacetylbaccatin III obtained from the leaves of yew and methods for mass production thereof based on cell culture technique of yew have been developed.

In addition, 13-dehydroxybaccatin III and 10-deacetylpaclitaxel can be used as important precursors for paclitaxel [Rao K V, Bhakuni R S, Johnson J, Oruganti R S., Synthesis and evaluation of some 10-mono- and 2',10-diesters of 10-deacetylpaclitaxel. J. med. Chem., 1995, 38, 3411-3414.; Ojima I, Sun C M, Zucco M, Park Y H, Duclos O, Kuduk S, A highly efficient route to taxoter by the β-lactam synthon method. Tetrahedron Lett., 1993, 34, 4149-4152.; Commercon A, Bezard D, Bernard F, Bourzat J D., Improved protection and esterification of a precursor of the Taxotere and taxol side chains. Tetrahedron Lett., 1992, 33, 5185.; Holton R, "Method for preparation of Taxol using an oxazinone." European Patent Application 400, 971(1990), U.S. Pat. No. 5,015, 744(1991); "Method for preparation of taxol using β-lactam." European Patent Application 428,375(1991), U.S. Pat. No. 5,175,315(1992)], and these substances are co-produced along with paclitaxel during the course of production of paclitaxel by yew or yew cell cultures.

Separation and purification methods for 13-dehydroxybaccatin III and 10-deacetylpaclitaxel have not been widely known in documents, and in particular, no records can be found in the case of 13-dehydroxybaccatin III. In the case of 10-deacetylpaclitaxel, U.S. Pat. No. 5,475,120 discloses methods for extraction and purification of paclitaxel and several derivatives from yew. The process disclosed in this patent comprises obtaining several fractions using extraction, partition, and reverse phase chromatography using C-18 (15-35 micron) of preparative scale and then purifying useful components including paclitaxel, 10-deacetylbaccatin III and 10-deacetylpaclitaxel from each fraction. However, the C-18 resins are expensive as they are 15-35 micron, and the applied specimens are extracts, which can readily contaminate the C-18 resins, and thus, their durability can be shortened. Besides, as there have been no evaluation information relating to purity and yields according to each purification step, it is difficult to understand the efficiency of the process.

Further, Erik L. M. et al. published research results about the content analysis of paclitaxel, 10-deacetylpaclitaxel, baccatin III, etc. by using HPLC after extraction using organic solvents from several *Taxus* species and pre-treatment using solid phase extraction column (Phytochemistry, 53(2000) 383-389), but this method is suitable only for quantity analysis using HPLC, not for isolating useful components. No detailed information on mass purification for 10-deacetylpaclitaxel have yet been reported.

U.S. Pat. No. 6,002,025 discloses a method for purification by fraction collecting taxanes such as 10-deacetylpaclitaxel, baccatin III and paclitaxel of 50% or higher purity using phenylalkyl column and preparative HPLC; however, it is not a process which is related to extraction and isolation from yew or cultured yew cells. That is, the disclosed process is restricted to purifying partially-purified taxanes by using preparative HPLC.

Therefore, the development of efficient isolation and purification methods of 13-dehydroxybaccatin III and 10-deacetylpaclitaxel of high purity from taxane-containing materials is in need.

SUMMARY OF THE INVENTION

It is an object of the present invention to provide a method of efficiently separating and purifying 13-dehydroxybaccatin III and 10-deacetylpaclitaxel with high purity, thereby providing a large amount of them from taxane-containing materials, so that they can be usefully used as semi-synthetic precursors of paclitaxel and/or docetaxel which are anticancer agents.

BRIEF DESCRIPTION OF THE DRAWINGS

FIG. 2b to 2d show HPLC analysis chromatograms of active fraction of the liquid/liquid extraction dry matter which were separated by using normal phase chromatography, wherein

DETAILED DESCRIPTION OF THE PREFERRED EMBODIMENTS

A more complete appreciation of the invention, and many of the attendant advantages thereof, will be readily apparent as the same becomes better understood by reference to the following detailed description.

This invention is directed to a method of separating and purifying 13-dehydroxybaccatin III and 10-deacetylpaclitaxel with high purity of 90% or higher, preferably 99.5% or higher from taxane-containing materials, thereby obtaining highly pure 13-dehydroxybaccatin III and 10-deacetylpaclitaxel which are useful as semi-synthetic precursors of paclitaxel and/or docetaxel which are anticancer agents.

The 13-dehydroxybaccatin III and 10-deacetylpaclitaxel can be produced along with paclitaxel during the course of production of paclitaxel from *Taxus* species plants such as yew which are typical examples of the taxane-containing materials or by yew cell cultures.

Figure 1:
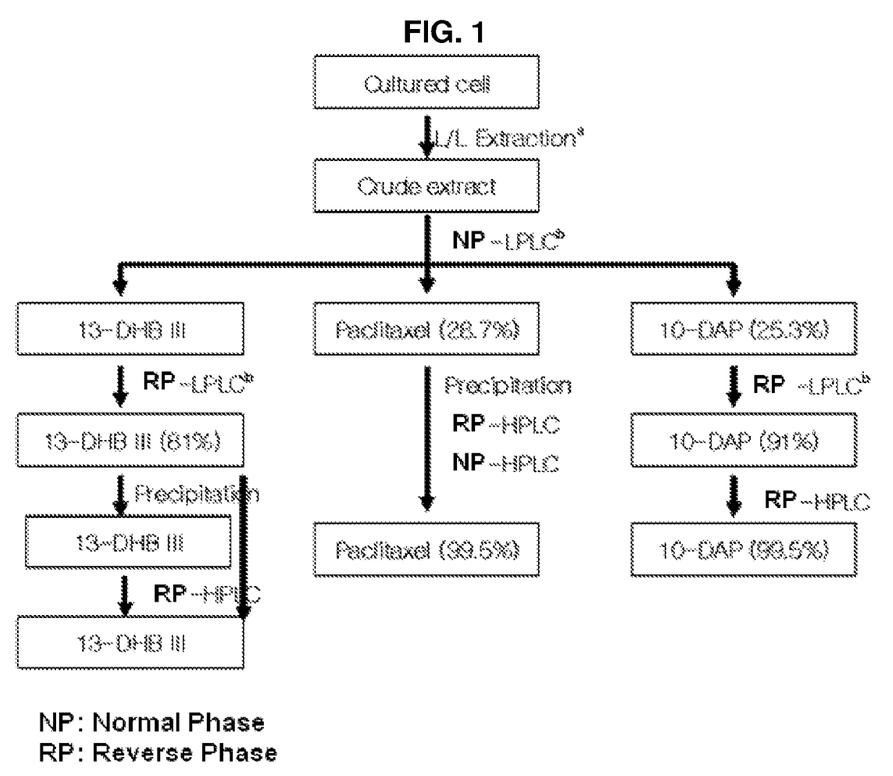
FIG. 1 is a schematic view showing separation and purification processes of 13-dehydroxybaccatin III (13-DHB III), paclitaxel and 10-deacetylpaclitaxel (10-DAP). [$^a$L/L (Liquid/liquid) Extraction; $^b$LPLC low pressure liquid chromatography)]
Figure 2A:
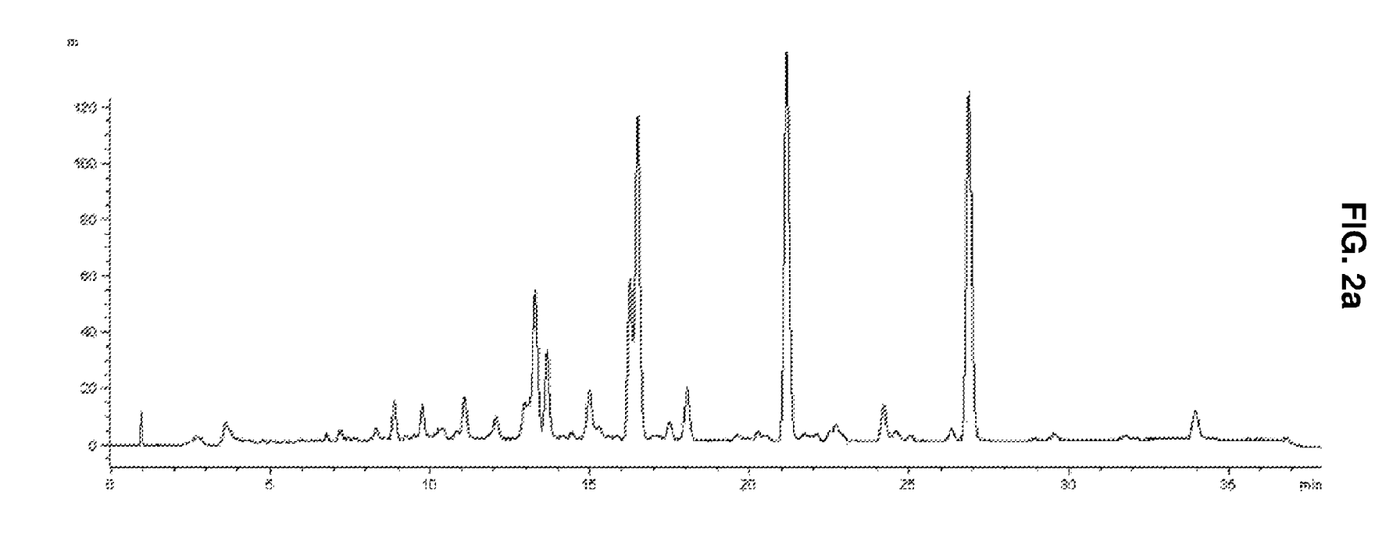
FIG. 2a shows an HPLC analysis chromatogram of extraction dry matter (liquid/liquid extracted dry matter) of Example 1 of the present invention.
Figure 2B:
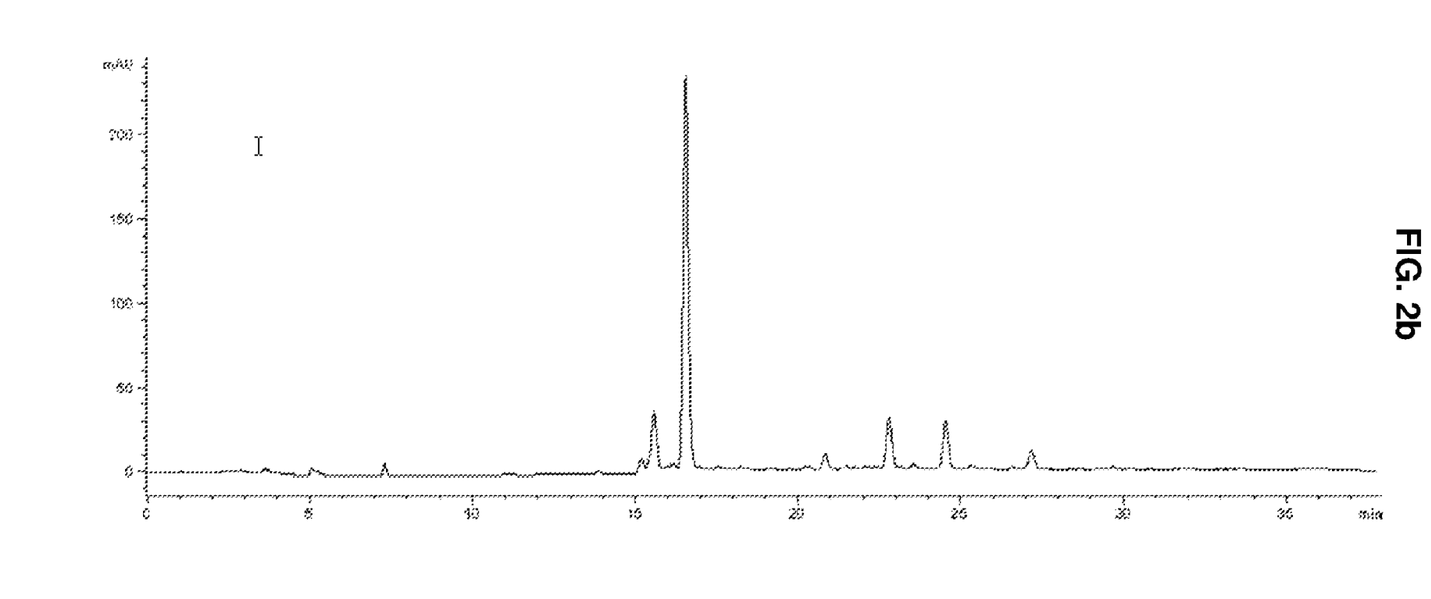
FIG. 2b represents 13-dehydroxybaccatin III active fraction.
Figure 2C:
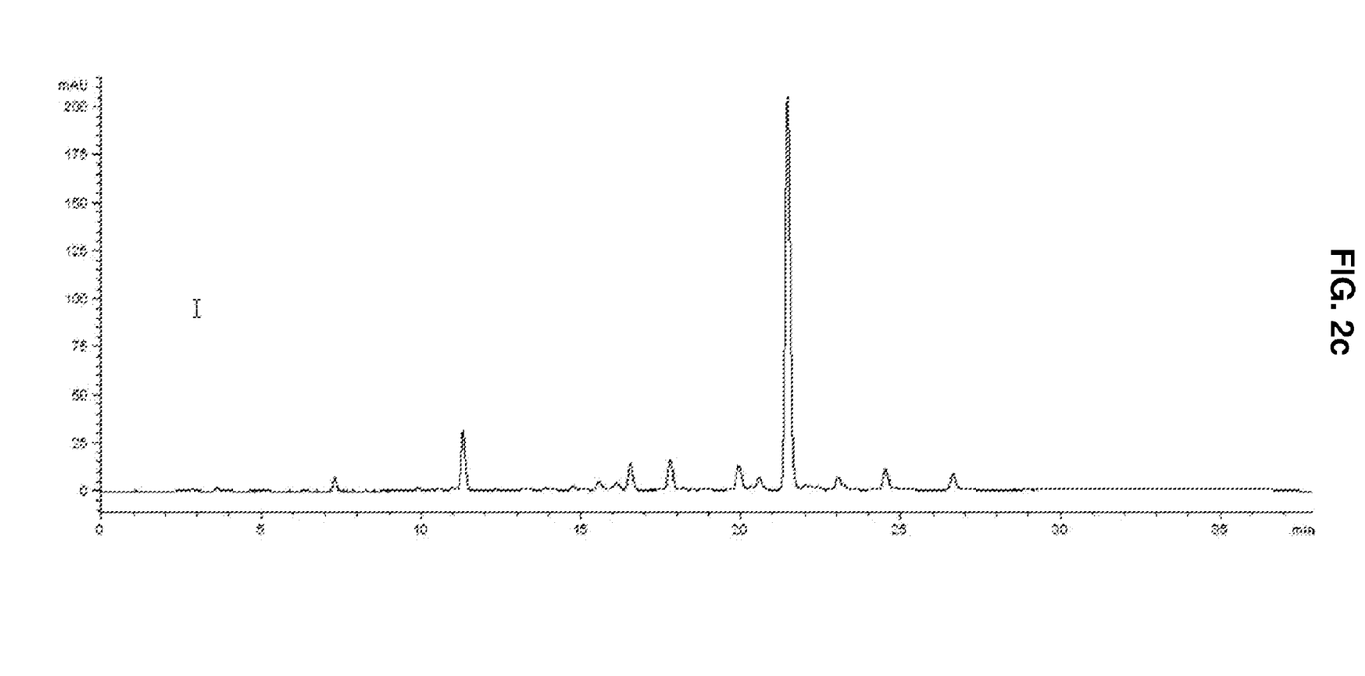
FIG. 2c represents paclitaxel active fraction and FIG. 2d represents 10-deacetylpaclitaxel fraction.
Figure 2D:
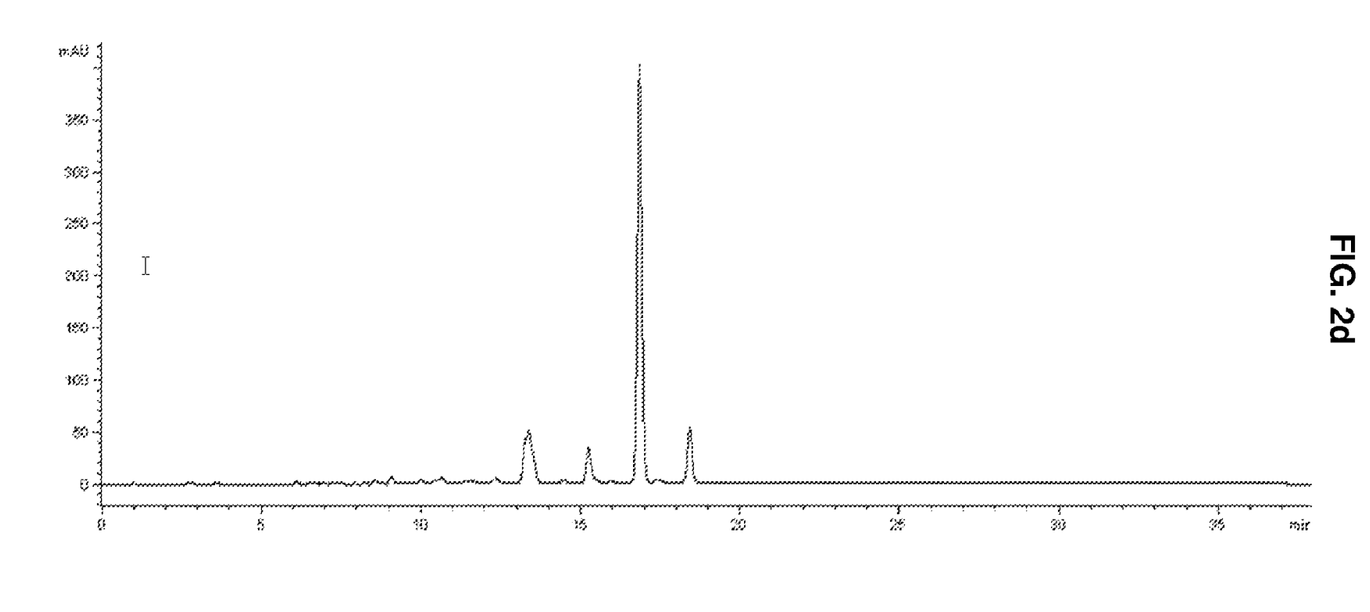
Figure 3:
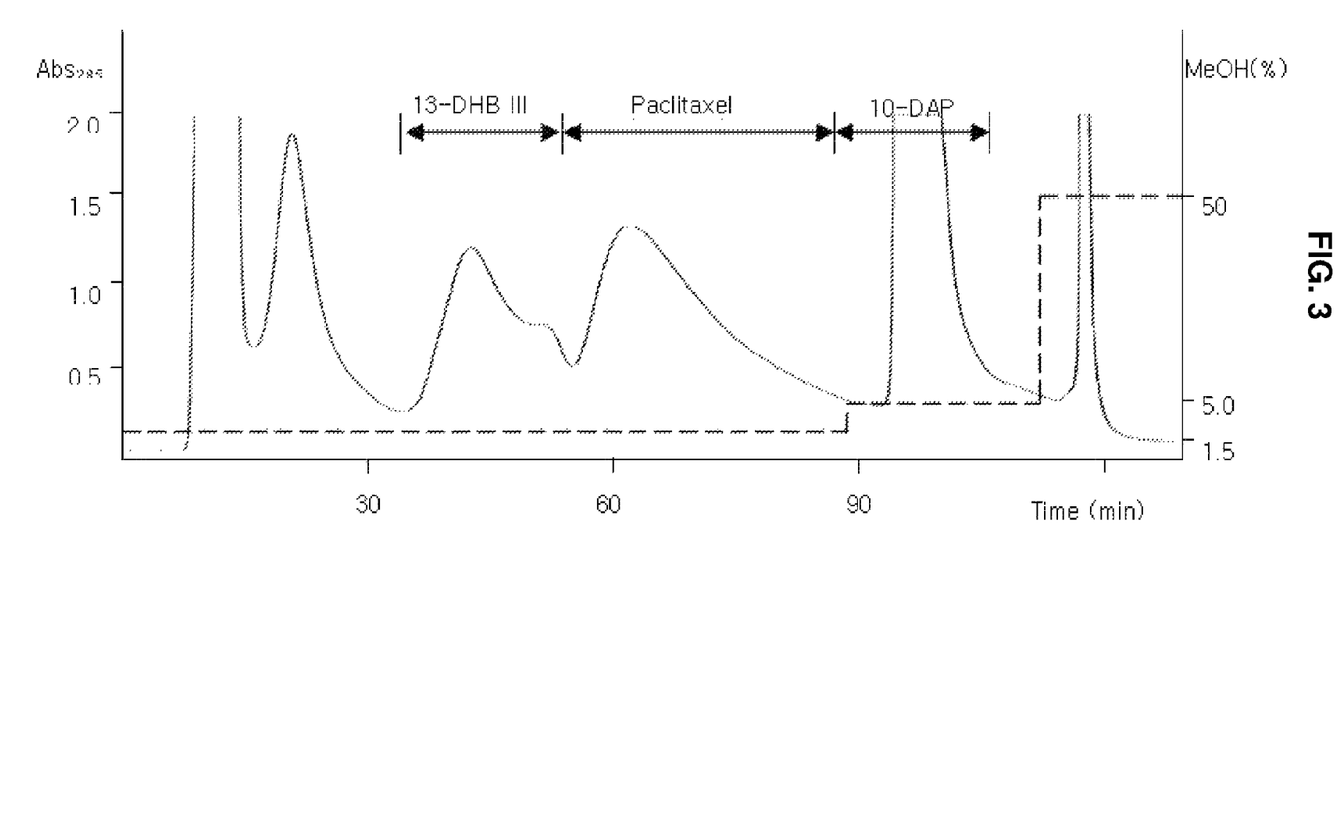
FIG. 3 shows a chromatogram of normal phase chromatography carried out in Example 2 of the present invention.
Figure 4:
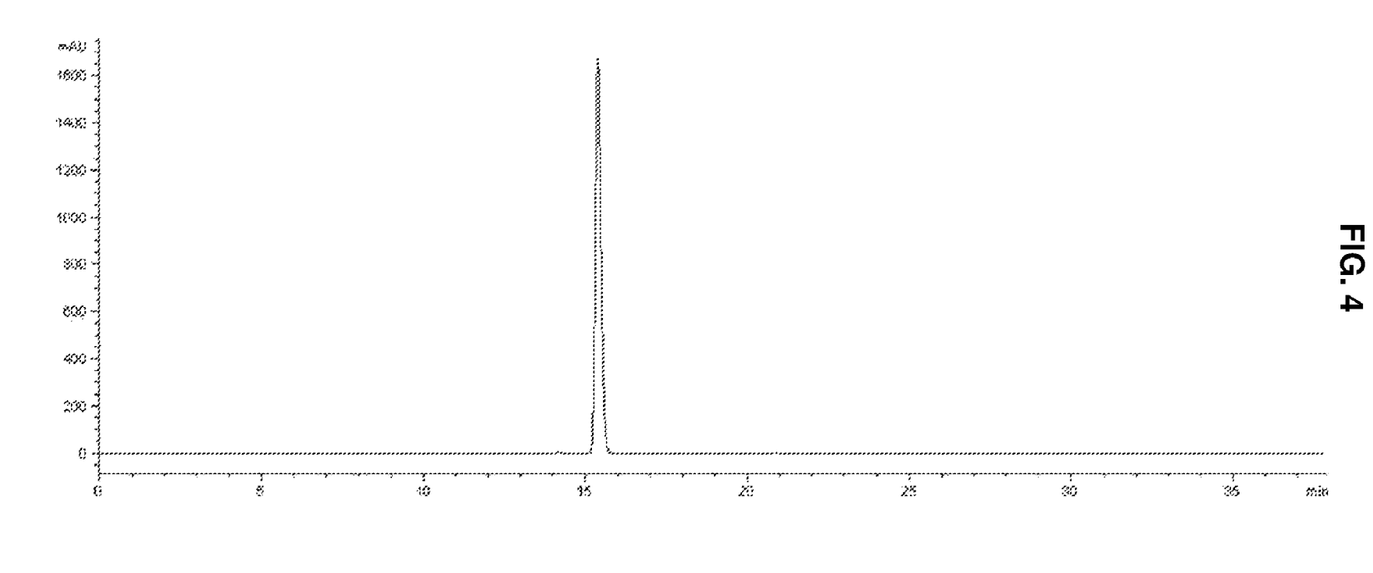
FIG. 4 shows an HPLC analysis chromatogram of 13-dehydroxybaccatin III purified in Example 5 of the present invention.
Figure 5:
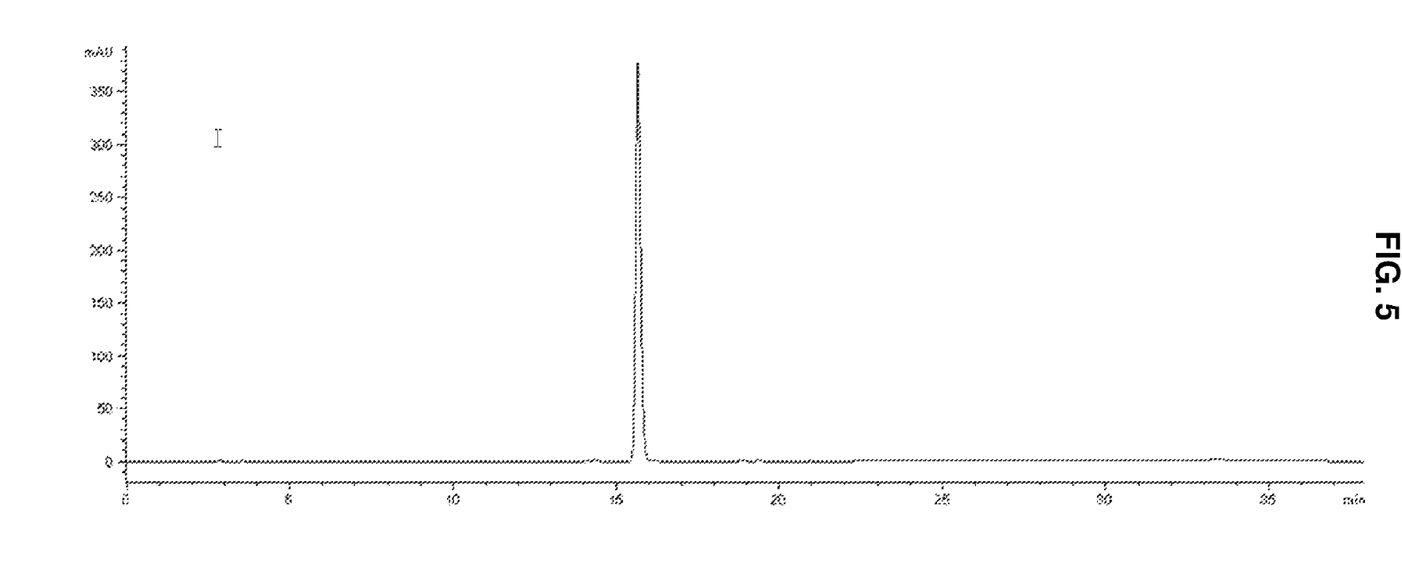
FIG. 5 shows an HPLC analysis chromatogram of 10-deacetylpaclitaxel purified in Example 7 of the present invention.

The separation and purification method of the present invention simultaneously provides separation of 13-dehydroxybaccatin III and 10-deacetylpaclitaxel active fraction that are useful as semi-synthetic precursors of paclitaxel and/or docetaxel as well as paclitaxel itself extracted from taxane-containing materials (see FIG. 1 and FIG. 2) by a single normal phase chromatography process from extracts. In addition, the separation and purification method also provides efficient purification of 13-dehydroxybaccatin III and 10-deacetylpaclitaxel by reverse phase low pressure chromatography of the obtained 13-dehydroxybaccatin III and 10-deacetylpaclitaxel active fractions.

First, this invention provides a method of separating and purifying 13-dehydroxybaccatin III from a taxane-containing material. The separation and purification method of 13-dehydroxybaccatin III of the invention comprises the following steps:

(a) extracting the taxane-containing material with an organic solvent and concentrating it (step of extraction and concentration of raw material);

(b) partitioning the concentration solution obtained from step (a) by addition of an organic solvent which is not mixable with water and liquid/liquid extracting the partitioned solution to separate the organic solvent layer therefrom (liquid/liquid extraction step);

(c) concentrating the extracted solution obtained from step (b) under reduced pressure, dissolving it in an organic solvent and performing normal phase low-pressure liquid chromatography to obtain paclitaxel, 13-dehydroxybaccatin III and 10-deacetylpaclitaxel active fractions at the same time (fraction step by normal phase chromatography); and (d-1) dissolving the 13-dehydroxybaccatin III active fraction obtained from the normal phase chromatography in step (c) in an organic solvent, and performing reverse phase low-pressure liquid chromatography to obtain 13-dehydroxybaccatin III active fraction. The extraction and purification method of the present invention can provide 13-dehydroxybaccatin III with 80% or higher purity, the precursor purity of which is sufficient for semi-synthesis, and more preferably 90% or higher purity can be provided.

In order to obtain 13-dehydroxybaccatin III with higher purity, the separation and purification method of 13-dehydroxybaccatin III can further comprise the step of precipitating the 13-dehydroxybaccatin III active fraction obtained from the reverse phase low-pressure liquid chromatography (RP-LPLC) using an organic solvent, purified water or mixture thereof to obtain 13-dehydroxybaccatin III-containing precipitate (precipitation formation step).

Also, it may further comprise the step of performing reverse phase high performance liquid chromatography (RP-HPLC) of the 13-dehydroxybaccatin III active fraction obtained from step (d-1) or the 13-dehydroxybaccatin III-containing precipitate obtained from the additional precipitation formation step.

By carrying out such additional steps of precipitation formation and/or reverse phase high performance liquid chromatography, 13-dehydroxybaccatin III with high purity of 99.5% or higher purity can be obtained.

Also, the invention provides a method of separating and purifying 10-deacetylpaclitaxel from a taxane-containing material. The separation and purification method of 10-deacetylpaclitaxel of the invention comprises the following steps:

(a) extracting the taxane-containing material with an organic solvent and concentrating it (step of extraction and concentration of raw material);

(b) partitioning the concentrated solution obtained from step (a) by addition of an organic solvent which is not mixable with water, and liquid/liquid extracting the partitioned solution to separate the organic solvent layer therefrom (liquid/liquid extraction step);

(c) concentrating the extracted solution resulted from step (b) under reduced pressure, dissolving it in an organic solvent and performing normal phase low-pressure liquid chromatography to obtain paclitaxel, 13-dehydroxybaccatin III and 10-deacetylpaclitaxel active fractions at the same time (fraction step by normal phase chromatography); and (d-2) dissolving the 10-deacetylpaclitaxel active fraction obtained from the normal phase chromatography in step (c) in an organic solvent, and performing reverse phase low-pressure liquid chromatography to obtain 10-deacetylpaclitaxel active fraction.

Such extraction and purification method can provide 10-deacetylpaclitaxel with 80% or higher purity, the precursor purity of which is sufficient for semi-synthesis, and more preferably 90% or higher purity can be provided.

In order to obtain 10-deacetylpaclitaxel with higher purity, the separation and purification method of 10-deacetylpaclitaxel can further comprise performing reverse phase high performance liquid chromatography of the 10-deacetylpaclitaxel obtained from step (d-2). By such additional performance of reverse phase high performance liquid chromatography, 10-deacetylpaclitaxel with high purity of 99.5% or higher purity can be obtained.

Also, the invention provides a method of separating and purifying 13-dehydroxybaccatin III and 10-deacetylpaclitaxel from a taxane-containing material by performing separation and purification of the 13-dehydroxybaccatin III and separation and purification of 10-deacetylpaclitaxel simultaneously or successively. The separation and purification method of the present invention comprises the following steps:

(a) extracting the taxane-containing material with an organic solvent and concentrating it (step of extraction and concentration of raw material);

(b) partitioning the concentrated solution obtained from step (a) by addition of an organic solvent which is not mixable with water, and liquid/liquid extracting the partitioned solution to separate the organic solvent layer therefrom (liquid/liquid extraction step);

(c) concentrating the extracted solution obtained from step (b) under reduced pressure, dissolving it in an organic solvent and performing normal phase low-pressure liquid chromatography to obtain paclitaxel, 13-dehydroxybaccatin III and 10-deacetylpaclitaxel active fraction at the same time (fraction step of normal phase chromatography); and (d) a step of separating and purifying 13-dehydroxybaccatin III and 10-deacetylpaclitaxel from the 13-dehydroxybaccatin III and 10-deacetylpaclitaxel active fraction obtained from the normal phase chromatography in step (c) comprising:

(d-1) 1) dissolving the 13-dehydroxybaccatin III active fraction obtained from the normal phase chromatography in step (c) in an organic solvent and performing reverse phase low-pressure liquid chromatography to obtain 13-dehydroxybaccatin III active fraction;

2) optionally, precipitating the 13-dehydroxybaccatin III active fraction obtained by reverse phase chromatography using purified water or organic solvent to obtain 13-dehydroxybaccatin-containing precipitate; and 3) optionally, performing reverse phase high-performance liquid chromatography of the 13-dehydroxybaccatin III active fraction obtained by reverse phase chromatography or the 13-dehydroxybaccatin-containing precipitate; and (d-2) 1) dissolving the 10-deacetylpaclitaxel active fraction obtained from the normal phase chromatography in step (c) in an organic solvent, and performing reverse phase low-pressure liquid chromatography to obtain 10-deacetylpaclitaxel active fraction; and 2) optionally, performing reverse phase high-performance liquid chromatography of the 10-deacetylpaclitaxel active fraction obtained by reverse phase chromatography.

The separation and purification method of the present invention described above is depicted in FIG. 1 in a simple way.

According to the present invention, 13-dehydroxybaccatin III and 10-deacetylpaclitaxel that are useful as precursors of paclitaxel or docetaxel, along with paclitaxel can be simultaneously separated by a single process in the course of the separation and purification process of paclitaxel that is used as an anticancer agent. Hence, additional culture costs and extraction and separation costs can be saved for the production of these useful components, and as the methods of the present invention use low pressure chromatography which employs very inexpensive silica, mass production in industrial scales can be possible. In particular, the reverse phase low pressure liquid chromatography process of the present invention can use C-18 resins, which are approximately 100 micron, have low processing pressure and are relatively inexpensive. Further, additional effects such as the decrease of facility scale and recycle after distillation can be expected by, as the solvent used in the reverse phase low pressure liquid chromatography, using the same solvent as one used in the subsequent high performance liquid chromatography process.

Also, another advantage to the present invention is that the separation and purification of 13-dehydroxybaccatin III and 10-deacetylpaclitaxel that are useful as precursors of paclitaxel or docetaxel, in highly pure form of 80% or higher purity which is easy of synthesis, preferably 90% or higher, and more preferably 99.5% are possible.

The "taxane-containing material" used as a starting material to obtain 13-dehydroxybaccatin III and 10-deacetylpaclitaxel in the present invention refers to *Taxus* genus plant body, or cell cultures including culture media, cells or tissues cultured using *Taxus* genus plant body-derived cells. Examples of the *Taxus* genus plant body include *Taxus brevifolia, Taxus canadensis, Taxus cuspidate, Taxus baccata, Taxus globosa, Taxus floridana, Taxus wallichiana, Taxus media* and *Taxus chinensis*.

Hereafter, the above-discussed process will be described in more detail.

(a) Step of Extraction and Concentration of Raw Material

For the organic solvent to be added to the taxane-containing materials in step (a), low molecular alcohols (C1-C4) such as methanol, ethanol or propanol, or halogenated alkanes (C1-C2) such as dichloromethane or chloroform and preferably, methanol can be used. When extracting with methanol, after methanol is added in an amount of 20 to 200% (v/v) of the taxane-containing materials, preferably 40 to 140% (v/v), it is agitated at room temperature for 30 minutes and then is filtrated two or more times, thereby extracting paclitaxel and taxane derivatives. The extracted solution obtained is evaporated in bath of 35 to 40° C. under reduced pressure so that the volume of the concentration solution becomes ⅕ to 1/20 times, preferably ⅛ to 1/12 times. This is equally applied to the concentration process to be followed.

(b) Liquid/Liquid Extraction Step

In step (b), an organic solvent which is not mixable with water is added to the concentrate obtained from step (a) in an amount of 10% to 50% (v/v), preferably 20% to 30% (v/v), stirred and partitioned and then, the organic solvent layer is separated and repeatedly concentrated under reduced pressure and then is dried two or more times. If the amount of the organic solvent to be added is 10% (v/v) or less, the above step is repeated more times and the separation of layers does not occur well. However, if 50% (v/v) or more of the organic solvent is added, the amount of the solvent to be used is increased while the purity of the obtained product tend to decrease. Accordingly, considering the yield, purity and solvent amount in this extraction step, the organic solvent can be added in 10% to 50% (v/v), preferably 20% to 30% (v/v). Examples of the organic solvent which is not mixable with water are halogenated alkanes (C1-C2) such as dichloromethane or chloroform, ethers such as ethyl ether, ethyl acetate, butanol, etc. Further, this step partially eliminates polar substances.

(c) Step of Partition by Normal Phase Chromatography

In step (c), the extraction solution obtained from step (b) can be purified by using normal phase low pressure liquid chromatography. In case of the purification by normal phase chromatography, silica gel can be used as the filler of columns and for example, silica gel 40 (63~200 μm), silica gel 60(63~200 μm), or silica gel 60F254(200~500 μm), preferably silica gel 60, can be used. As a development solvent, halogenated alkanes (C1-C2) such as dichloromethane or chloroform, organic solvents such as methanol, benzene, acetone, hexane or ethyl acetate, or mixture solutions thereof can be used. Preferably, for the performance of more efficient chromatography, by using isocratic or step elution methods, 0.5% (v/v) to 10% (v/v), and more preferably 1.0% (v/v) to 5% (v/v), methanol/dichloromethane mixture solution can be used, This process allows simultaneous separation of paclitaxel, 13-dehydroxybaccatin III and 10-deacetylpaclitaxel.

(d) Step of Extraction and Purification of 13-dehydroxybaccatin III and 10-Deacetylpaclitaxel by Reverse Phase Chromatography In step (d), after the 13-dehydroxybaccatin III and 10-deacetylpaclitaxel active fractions obtained from step (c) are concentrated and then dried, reverse phase column chromatography is carried out such that 13-dehydroxybaccatin III and 10-deacetylpaclitaxel can be purified with high purity and high yield from each active fraction.

(d-1) Extraction and Purification of 13-dehydroxybaccatin III

The extraction and purification of 13-dehydroxybaccatin III from the 13-dehydroxybaccatin III active fraction are as follows.

1) Reverse phase low pressure liquid chromatography is carried out on the 13-dehydroxybaccatin III active fraction obtained from step (c) wherein as the filler of column, ordinary hydrophobic resins 63~200 μm ODS (Octadecylsilylated, C18), C8 or C4 can be used. As a development solvent, alcohols (C1-C6) such as methanol, ethanol and propanol, organic solvents such as acetonitrile, purified water or mixture solutions thereof can be used. Preferably, for the performance of more efficient chromatography, by using isocratic or step elution methods, 20% (v/v) to 90% (v/v) methanol/purified water mixture solution, more preferably 50.0% (v/v) to 75% (v/v) methanol/purified water mixture solution, can be used.

2) Optionally, after the 13-dehydroxybaccatin III active fraction obtained from the reverse phase chromatography is concentrated and dried by evaporating in water bath of 35~40° C. under reduced pressure, dry matters are withdrawn and dissolved in an organic solvent, to which a precipitation-forming solvent is then added in an amount of 1 to 20 times, preferably 3 to 10 times, of the volume of the organic solvent used in the dry matter dissolution, thereby forming precipitation, and then filtration step can be carried out. As the organic solvent used in the dissolution of the dry matters, halogenated alkanes (C1-C2) such as tetrahydrofuran, dichlorormethane and chloroform, low molecular alcohols (C1-C4) such as methanol, ethanol or propanol, ketones, etc., and preferably, tetrahydrofuran can be used. For the precipitation-forming solvent, organic solvents such as C4 to C8 alkanes, purified water or mixtures thereof can be used. When the amount of the precipitation-forming solvent to be added is equal to or less than the volume of the organic solvent, precipitation does not form well, and when it is 20 times or more, the amount of the solvent to be used is too excessive and filtration time is increased.

The precipitation time and storage temperature are not specifically limited, and the precipitation can be carried out by letting it stay for 1 to 5 days, preferably for 1 day or 2 days and the storage temperature can be 35° C. or below, preferably −20 ° C. to 15° C. In general, precipitation formation is completed within 1 to 2 days, but at temperatures of 35° C. or higher, precipitation formation does not occur well and the degradation of specimen may be generated and at temperatures of −20° C. or lower, the precipitation of impurities is induced and purity can thus be lowered.

3) Optionally, the 13-dehydroxybaccatin III active fraction by reverse phase chromatography or the 13-dehydroxybaccatin III precipitate obtained from the above can be subject to purification process by high performance liquid chromatography. The high performance liquid chromatography can be filled with ordinary hydrophobic resins that allow the elimination of non polar impurities, 5 to 100 μm, preferably 10 to 50 μm ODS (Octadecylsilylated, C18), C8 or C4. As a development solution, alcohols (C1-C4) such as methanol, ethanol and propanol, organic solvents such as acetonitrile, purified water or mixture solutions thereof can be used, and preferably, 50 to 75% (v/v) methanol/purified water mixture solution can be used.

If 13-dehydroxybaccatin III is separated and purified by using the method described above, highly pure 13-dehydroxybaccatin III with 99.5% or higher purity can be obtained with high yield of 61.7% to 79.9% yield.

The purity and recovery rate ranges of 13-dehydroxybaccatin III that can be obtained by using the above process are shown in Table 1.

TABLE 1

| | Purity of Dry Matter (%) | Recovery Rate (%) |
|---|---|---|
| Starting 13-dehydroxybaccatin III Containing Material | 0.01-0.05 | 100 |
| Methanol Extraction | 0.05-0.5 | 93-97 |
| Liquid/Liquid Extraction | 1.0-9.0 | 94-96 |
| Normal Phase Liquid Chromatography | 10-35 | 95-97 |
| Reverse Phase Liquid Chromatography | 65-90 | 95-97 |
| Tetrahydrofuran/Hexane Precipitation | 90-99 | 85-95 |
| Reverse Phase High Perfomance Liquid Chromatography | 99.5-99.9 | 92-96 |
| Total | 99.5-99.9 | 61.7-79.9 |

(d-2) Extraction and Purification of 10-Deacetylpaclitaxel

The extraction and purification process of 10-deacetylpaclitaxel from the 10-deacetylpaclitaxel active fraction obtained from step (c) is as follows:

1) The 10-deacetylpaclitaxel active fraction obtained from step (c) is evaporated in water bath of 35 to 40° C. under reduced pressure and dried and then reverse phase low pressure liquid chromatography is carried out. As the filler of the reverse phase low pressure liquid chromatography, ordinary hydrophobic resins, 63~200 μm ODS (Octadecylsilylated, C18), C8 or C4 can be used. As a development solvent, alcohols of C1-C6 such as methanol, ethanol and propanol, organic solvents such as acetonitrile, purified water or mixture solution thereof can be used. Preferably, for the performance of more efficient chromatography, by using isocratic or step elution methods, 20% (v/v) to 90% (v/v), more preferably 50.0% (v/v) to 75% (v/v), methanol/purified water mixture solution can be used.

2) Optionally, the 10-deacetylpaclitaxel active fraction obtained from the reverse phase chromatography is evaporated in water bath of 35 to 40° C. under reduced pressure and then high-performance liquid chromatography is performed. The high-performance liquid chromatography can be filled with ordinary hydrophobic resins that allow the elimination of non-polar impurities, such as 5 to 100 μm, preferably 10 to 50 μm ODS (Octadecylsilylated, C18), C8 or C4. As a development solution, alcohols such as methanol, ethanol and propanol, organic solvents such as acetonitrile, purified water or mixture solutions thereof can be used and preferably, 50 to 75% (v/v) methanol/purified water mixture solution is used as a development solution for the performance of more efficient chromatography.

In accordance with the subject invention, highly pure 10-deacetylpaclitaxel with 99.5% or higher purity can be obtained with a high yield of 72.6% to 84.1% by a relatively simple process.

The purity and recovery rate ranges of 10-deacetylpaclitaxel that can be obtained by using the above process are shown in Table 2.

TABLE 2

| | Purity of Dry Matter (%) | Recovery Rate (%) |
|---|---|---|
| Starting 10-deacetylpaclitaxel Containing Material | 0.01-0.05 | 100 |
| Methanol Extraction | 0.05-0.5 | 93-97 |
| Liquid/Liquid Extraction | 1.0-9.0 | 94-96 |
| Normal Phase LIquid Chromatography | 10-35 | 95-97 |

TABLE 2-continued

|  | Purity of Dry Matter (%) | Recovery Rate (%) |
|---|---|---|
| Reverse Phase LIquid Chromatography | 75-95 | 95-97 |
| Reverse Phase High Performance Liquid Chromatography | 99.5-99.9 | 92-96 |
| Total | 99.5-99.9 | 72.6-84.1 |

The purity and recovery rate of paclitaxel isolated from step (c) are calculated by quantity analysis using HPLC with the conditions of Table 3.

TABLE 3

| Apparatus | Hewlett Packard 1090 HPLC |
|---|---|
| Column | Curosil PFP 4.6 × 250 mm |
| Column Temperature | 35° C. |
| Mobile Phase | Acetonitrile: Water (35-65%(v/v) Concentration Gradient) |
| Flow Rate | 1 ml/min. |
| Injection Amount | 10 ul |
| Detector | UV(227 nm) |

The present invention is further explained in more detail with reference to the following examples. These examples, however, should not be interpreted as limiting the scope of the present invention in any manner.

EXAMPLE 1

Organic Solvent Extraction and Liquid/Liquid Extraction of Plant Cell Culture Media 55 L of methanol was added to 50kg of plant cells obtained from the cell culture of *Taxus chinensis*-derived cell line (SYG-1, KCTC-0232BP) as described in Korean Patent Laid-Open No. 2005-0069891, and then, it was agitated at room temperature for 30 min. and filtration step was repeated four times, thereby obtaining methanol extraction solution, which was then concentrated into approximately 10 L under reduced pressure. 2800 ml of dichloromethane was added to the concentrate, which was then partitioned by stirring with 120 rpm for 30 minutes. Then, after the dichloromethane layer is separated, it was dried by evaporating in water bath of 35 to 40° C. under reduced pressure, thereby obtaining 385 g of liquid/liquid extraction dry matters including 13-dehydroxybaccatin III with a purity of 2.7%, 10-deacetylpaclitaxel with a purity of 4.2% and paclitaxel with a purity of 5.8%.

EXAMPLE 2

Normal Phase Liquid Chromatography, Isocractic Elution, and Step Elution

After 300 g of the dry matters obtained from Example 1 was dissolved with 4000 ml of dichloromethane and then filtrated, it was applied to isocratic method where 1.5% (v/v) methanol/dichloromethane was eluted continuously without changing the solvent in columns made of stainless steel having diameter of 19 cm and length of 90 cm filled with silica gel 60N (Timely Co. Ltd, Japan) filled up with 1.5% (v/v) methanol/dichloromethane. 13-dehydroxybaccatin III and paclitaxel were eluted using 1.5% (v/v) methanol/dichloromethane as an elution solvent and 10-deacetylpaclitaxel was step-eluted using 5.0% (v/v) methanol/dichloromethane elution solvent to obtain each active fraction and the analysis results are shown in Table 4 below.

TABLE 4

| Exp. No. | Active Fraction | Purity (%) | Recovery Rate (%) |
|---|---|---|---|
| A | 13-dehydroxybaccatin III | 21.5 | 97.5 |
| B | 10-deacetylpaclitaxel | 26.0 | 97.8 |
| C | Paclitaxel | 32.5 | 98.0 |

EXAMPLE 3

Purification of 13-dehydroxybaccatin III 3-1. Reverse Phase Low Pressure Liquid Chromatography, Isocractic Elution After the active fraction of Experiment Number A of Example 2 was dried by evaporating in water bath of 35 to 40° C. under reduced pressure and dissolved in 70% (v/v) methanol/purified water, chromatography by isocratic method was carried out using low pressure reverse phase liquid chromatography filled with ODS and 62% (v/v) methanol/purified water as a development solvent, thereby obtaining 13-dehydroxybaccatin III active fraction having a purity of 81% with a yield of 97.5%.

3-2. Tetrahydrofuran/Hexane Precipitation

Tetrahydrofuran/hexane precipitation process was carried out using the dry matter which was obtained by concentrating the active fraction obtained from Example 3-1 under reduced pressure and drying it at 0° C. for 24 hours. The dry matter was dissolved in tetrahydrofuran(THF) of the same amount and the precipitation process was performed under the following conditions: hexane ratio to tetrahydrofuran being 4.5 to 6.5 and the amount of specimen to tetrahydrofuran 10 ml being 0.5 g to 2.5 g. The obtained results are shown in Table 5 below.

TABLE 5

| | Starting Material | | | Precipitation | |
|---|---|---|---|---|---|
| Exp. No. | Purity (%) | Amount of Specimen (g) | THF (ml) | Hexane (ml) | Purity (%) | Yield (%) |
| D | 81 | 1.0 | 10 | 45 | 99.1 | 87.0 |
| E | 81 | 1.0 | 10 | 55 | 99.0 | 92.8 |
| F | 81 | 1.0 | 10 | 65 | 97.0 | 93.0 |
| G | 81 | 0.5 | 10 | 55 | 99.2 | 90.2 |
| H | 81 | 1.5 | 10 | 55 | 98.3 | 93.5 |
| I | 81 | 2.5 | 10 | 55 | 94.5 | 94.6 |

3-3. Reverse Phase High Performance Liquid Chromatography

After the precipitates of Experiment Number E of Example 3-2 were dried by evaporating in water bath of 40° C. under reduced pressure and then dissolving in 80% (v/v) methanol/purified water, chromatography by isocratic method using reverse phase high performance liquid chromatography filled with ODS and 65% (v/v) methanol/purified water as a development solvent was carried out, thereby obtaining 13-dehydroxybaccatin III having a purity of 99.5% with a yield of 96.5%.

EXAMPLE 4

Purification of 10-Deacetylpaclitaxel 4-1. Reverse Phase Low Pressure Liquid Chromatography, Isocratic Elution After the active fraction of Experiment Number B of Example 2 was dried by evaporating in water bath of 35° C. under reduced pressure and dissolving in 70% (v/v) methanol/purified water, chromatography by isocratic method using reverse phase low pressure liquid chromatography filled with ODS and 62% (v/v) methanol/purified water as a development solvent was carried out, thereby obtaining 10-deacetylpaclitaxel having a purity of 90.5% with a yield of 93.3%.

4-2. Reverse Phase High Performance Liquid Chromatography

After the active fraction of Example 4-1 was dried by being evaporated in water bath of 40° C. under reduced pressure and dissolved in 80% (v/v) methanol/purified water, chromatography by isocratic method using reverse phase low pressure liquid chromatography filled with ODS and 65% (v/v) methanol/purified water as a development solvent was carried out, thereby obtaining 10-deacetylpaclitaxel having a purity of 99.8% with a yield of 89%.

This invention is directed to the purification method of 13-dehydroxybaccatin III and 10-deacetylpaclitaxel and in accordance with the present invention, highly pure 13-dehydroxybaccatin III and 10-deacetylpaclitaxel having 99.5% or higher purity can be obtained. These substances can be usefully used as semi-synthetic precursors of paclitaxel and docetaxel. The purification method of the present invention is useful in producing 13-dehydroxybaccatin III and 10-deacetylpaclitaxel with a high yield and high purity by purifying them to have 80% or higher purity through extraction, normal phase and reverse phase low pressure liquid chromatography, and further, performing efficient purification in comparison with the prior art through tetrahydrofuran/hexane precipitation and high-performance liquid chromatography.

What is claimed is:

1. A method for separating and purifying 13-dehydroxybaccatin III and 10-deacetylpaclitaxel simultaneously from a taxane-containing material, the method comprising the steps of:
    (a) extracting the taxane-containing material with at least one organic solvent selected from the group consisting of low-molecular alcohols of C1 to C4 and halogenated alkanes (C1-C2), and concentrating the solvent including the extracted taxane-containing material;
    (b) partitioning the concentrated solution obtained from step (a) by adding at least one organic solvent selected from the group consisting of halogenated alkanes (C1-C2), ethers, ethyl acetate and butanol, that is not mixable with water, and liquid/liquid extracting the partitioned solution to separate an organic solvent layer of the at least one organic solvent selected from the group consisting of halogenated alkanes (C1-C2), ethers, ethyl acetate and butanol;
    (c) concentrating the extracted solution obtained from step (b) under reduced pressure, dissolving the concentrated solution in 0.5%(v/v) to 10%(v/v) methanol/dichloromethane mixture solution, and performing normal phase low-pressure liquid chromatography to obtain paclitaxel, 13-dehydroxybaccatin III and 10-deacetylpaclitaxel active fractions at the same time; and
    (d) as a step of separating and purifying 13-dehydroxybaccatin III and 10-deacetylpaclitaxel from the 13-dehydroxybaccatin III and 10-deacetylpaclitaxel active fractions obtained from the normal phase low-pressure liquid chromatography in step (c),
    (d-1) dissolving the 13-dehydroxybaccatin III active fraction obtained from the normal phase low-pressure liquid chromatography in step (c) in at least one organic solvent selected from the group consisting of alcohols of C1 to C4, acetonitrile, and purified water, and performing reverse phase low-pressure liquid chromatography to obtain 13-dehydroxybaccatin III active fraction; and
    (d-2) dissolving the 10-deacetylpaclitaxel active fraction obtained from the normal phase low-pressure liquid chromatography in step (c) in at least one organic solvent selected from the group consisting of alcohols of C1 to C4, acetonitrile, and purified water, and performing reverse phase low-pressure liquid chromatography to obtain 10-deacetylpaclitaxel active fraction.

2. The method according to claim 1 further comprising, after the performing the reverse phase low-pressure liquid chromatography of step (d-1), at least one step of:
    precipitating the 13-dehydroxybaccatin III active fraction obtained from the reverse phase low-pressure liquid chromatography using an organic solvent, purified water or mixture thereof to obtain 13-dehydroxybaccatin III-containing precipitates; and
    performing reverse phase high performance liquid chromatography.

3. The method according to claim 2, wherein the step of obtaining the precipitates comprises:
    dissolving the 13-dehydroxybaccatin III active fraction by reverse phase chromatography using an organic solvent selected from the group consisting of tetrahydrofuran, alcohols of C1 to C4, halogenated alkanes of C1 to C2, ketones, and mixtures thereof; and
    adding to the obtained solution a substance selected from the group consisting of alkanes of C4 to C8, purified water and mixtures thereof in a volume of 1 to 20 times of the volume of the solvent used for dissolving the 13-dehydroxybaccatin III active fraction to form precipitation.

4. The method according to claim 1 further comprising, after performing the reverse phase low-pressure liquid chromatography of step (d-2), the step of performing reverse phase high performance liquid chromatography of the obtained 10-deacetylpaclitaxel active fraction.

5. The method according to claim 1, wherein the taxane-containing material is *Taxus* species plant body selected from the group consisting of *Taxus brevifolia, Taxus canadensis, Taxus cuspidate, Taxus baccata, Taxus globosa, Taxus floridana, Taxus wallichiana, Taxus media* and *Taxus chinensis*, or a cell, tissue or cell culture derived from the *Taxus* species plant body.

* * * * *